United States Patent
Salmonsen et al.

(10) Patent No.: US 7,963,905 B2
(45) Date of Patent: Jun. 21, 2011

(54) CONTROL SYSTEM FOR A BLOOD PUMP

(75) Inventors: Robert Salmonsen, Kew (AU); David Mason, Balwyn North (AU); Peter John Ayre, Crows Nest (AU)

(73) Assignee: Thoratec Corporation, Pleasanton, CA (US)

( * ) Notice: Subject to any disclaimer, the term of this patent is extended or adjusted under 35 U.S.C. 154(b) by 865 days.

(21) Appl. No.: 11/973,877

(22) Filed: Oct. 10, 2007

(65) Prior Publication Data
US 2009/0099406 A1  Apr. 16, 2009

(30) Foreign Application Priority Data

Oct. 11, 2006 (AU) .................................. 2006905663

(51) Int. Cl.
*A61M 1/12* (2006.01)
(52) U.S. Cl. ............ 600/17; 600/16; 623/3.1; 623/3.28; 604/6.11
(58) Field of Classification Search .................. 604/6.11; 623/3.1, 3.28; 600/16, 17
See application file for complete search history.

(56) References Cited

U.S. PATENT DOCUMENTS

| | | | |
|---|---|---|---|
| 5,220,259 A | 6/1993 | Werner et al. | |
| 5,289,821 A | 3/1994 | Schwartz | |
| 5,888,242 A | 3/1999 | Antaki | |
| 6,027,498 A | 2/2000 | Mutch et al. | |
| 6,066,086 A | 5/2000 | Antaki | |
| 6,068,588 A | 5/2000 | Goldowsky | |
| 6,071,093 A | 6/2000 | Hart | |
| 6,183,412 B1 | 2/2001 | Benkowski et al. | |
| 6,227,797 B1 | 5/2001 | Watterson et al. | |
| 6,277,078 B1 | 8/2001 | Porat et al. | |
| 6,395,026 B1 | 5/2002 | Aboul Hosn et al. | |
| 6,443,983 B1 | 9/2002 | Nagyszalanczy et al. | |
| 6,572,530 B1 | 6/2003 | Araki et al. | |
| 6,623,420 B2 | 9/2003 | Reich et al. | |
| 6,709,382 B1 | 3/2004 | Horner | |
| 6,783,328 B2 | 8/2004 | Lucke et al. | |
| 6,949,066 B2 | 9/2005 | Bearnson et al. | |
| 6,991,595 B2 | 1/2006 | Burke et al. | |
| 7,138,776 B1 | 11/2006 | Gauthier et al. | |
| 7,141,943 B2 | 11/2006 | Song et al. | |
| 7,494,459 B2 | 2/2009 | Anstadt et al. | |
| 7,645,225 B2 | 1/2010 | Medvedev et al. | |
| 2001/0009645 A1 | 7/2001 | Noda | |
| 2002/0183628 A1 | 12/2002 | Reich et al. | |
| 2004/0047736 A1 | 3/2004 | Nose et al. | |

(Continued)

FOREIGN PATENT DOCUMENTS

EP          1 354 606          10/2003

(Continued)

OTHER PUBLICATIONS

International search report for National App. 2006905663 completed on Feb. 23, 2007.

*Primary Examiner* — Carl H Layno
*Assistant Examiner* — Gary A Porter, Jr.
(74) *Attorney, Agent, or Firm* — Squire, Sanders & Dempsey (US) LLP (57) ABSTRACT

A method of controlling the speed of a blood pump, wherein the method includes the steps of deriving an estimated pulsatility index from speed, then deriving an estimated blood pressure from estimated pulsatility index; and maintaining target blood flow rate near to or at a preset value by adjusting the speed.

20 Claims, 7 Drawing Sheets

U.S. PATENT DOCUMENTS

| | | |
|---|---|---|
| 2004/0152944 A1 | 8/2004 | Medvedev et al. |
| 2005/0208095 A1 | 9/2005 | Hunter et al. |
| 2005/0215843 A1 | 9/2005 | Medvedev |
| 2006/0149331 A1 | 7/2006 | Mann et al. |

FOREIGN PATENT DOCUMENTS

| | | |
|---|---|---|
| WO | WO 01/05023 | 1/2001 |
| WO | WO 03/057280 A2 | 7/2003 |
| WO | WO 2004/028593 A1 | 4/2004 |

CONTROL SYSTEM FOR A BLOOD PUMP

FIELD OF THE INVENTION

The present invention relates to a system for controlling a rotary blood pump to minimize adverse patient reactions to these pumps.

BACKGROUND OF THE INVENTION

Blood pumps have been commonly used to provide mechanical support or assistance to the left ventricles of patients. Typically, the left ventricle is responsible for pumping blood into the aorta and throughout a majority of the patient's body. Ventricular assistance has been previously been provided by an implanted blood pump, such as the Ventrassist™ rotary blood pump described in U.S. Pat. No. 6,227,797—Watterson et al.

These blood pumps generally pump blood in parallel to the normal circulatory system by removing blood directly from the left ventricle and pumping into a portion of the aorta. Generally when such a blood pump is implanted, blood may flow or be pumped by both the left ventricle and the blood pump.

The speed of the implanted blood pump is preferably carefully monitored and controlled. Preferably, the pump and the respective controller should be able to adapt to changes in physiological demand for blood of the patient's body. Preferably, the blood pump should not be allowed to run so fast that the pump causes a suction event whereby the pump receives less blood flow and the contractile properties of the ventricle are effectively lost or diminished. In severe situations of a suction event, the ventricle wall is pulled over an inflow of the blood pump and may completely occlude blood flow.

In the past, if an implanted blood pump pumps blood at a too high rate, when compared to the left ventricle, the heart may experience arrhythmias. Additionally, if the pump is operating at a relative speed that is too low, when compared to the left ventricle, the patient may experience oedemas.

U.S. Pat. No. 6,949,066—Beamson et al discloses a pump control system for use with a centrifugal type blood pump of the kind used as a left ventricle assist device. The system includes a first sensor that detects at least one operational parameter of the pump; and a second sensor that detects and measures at least one physiological parameter of a patient implanted with the pump. This system fails to address situations wherein intermittent suction events are occurring to a patient implanted with a left ventricle assist device. Additionally, the addition of sensors to the system will add to its complexity and increase the likelihood of device failure.

U.S. Pat. No. 6,991,595—Burke et al describes an adaptive speed control for an implanted blood pump wherein the control is adapted to detect the onset of left ventricular collapse by deriving and monitoring a pulsatility index, and adjusting the pump speed to maintain the pulsatility index at a pump set-point. The pulsatility set-point is decreased incrementally when the onset of ventricular collapse has not been detected for a predetermined period of time. Experimentally, it has been found that pulsatility index is the most or preferred physiological characteristic for determining the imminence of a suction event.

U.S. Pat. No. 6,783,328—Lucke et al discloses a pump control system that monitoring flow and/or pressure of the pump output and decides whether the flow or pressure exceeds a critical level. If the critical level is exceeded the control system reduces the pumping speed by reducing the pump set-point. This system relies on the expectation that the all of the pressure and/or flow experienced by blood at the pump outlet is the solely the output of the pump, this system ignores other pumping elements such as the natural heart which is still capable of supplying a proportion of flow and pressure. The system also only detects whether the threshold flow or pressure values have been exceeded and does not detect or determine any suction events.

U.S. Pat. No. 5,888,242—Antaki discloses an automatic speed control system for implanted blood pump wherein the speed of the pump is incrementally increased and when the system detects the imminence of a suction event occurring to the left ventricle, the system decreases the pump speed by a predetermined amount. A disadvantage with this system is that when the system detects the imminence of a suction event, the system slows the pump and then gradually increases the speed until the imminence is detected again. Hence the system continually repeats the error despite its detection and this may be dangerous for the patient.

U.S. Pat. No. 6,066,086—Antaki discloses a further automatic speed control system for use with an implanted cardiac assist blood pump wherein the system operates in a manner to prevent the opening of aortic valve during the operation of the heart, once it has been implanted with a left ventricle assist device. Experimentally, and to the contrary the inventors of the invention described within the present specification have found that it is preferable to allow the aortic valve to open and close during the operation of a left ventricular assist device. Furthermore the system described in the disclosure of U.S. Pat. No. 6,066,086 does not measure or predict suction events.

U.S. Pat. No. 6,623,420—Reich et al discloses a system wherein an implanted blood pump is connected to a single blood pressure detector which is positioned in the inflow of the pump. The detector continuously detects blood pressure within the cannula and compares the detected blood pressure to a tabulated predicted blood pressure. The system then adjusts the pump speed to minimize the difference between the detected value and the predicted value. Suction events are not directly avoided by this system.

U.S. Pat. No. 6,443,983—Nagyszalancy et al discloses a pump speed control system wherein blood flow and pressure are both detected and measured and then used in a feedback to control speeds of two blood pumps. The system requires measured values for both flow and pressure to function and as such the system requires the additional implantation or use of sensors in the blood path, which is preferably avoided as they may lead to points of blood flow stagnation or blood clotting.

International Patent Publication No. WO 03/057013—Morello describes a control system for use with a blood pump. The system described within this disclosure is primarily reliant on a flow sensor included within the system. Generally, it has been found experimentally that sensors may increase the likelihood of device malfunction and/or reduce the overall biocompatibility of the system.

International Patent Publication No. WO 04/028593—Ayre describes a further control system for a rotary blood pump. However, this system generally includes a type of pressure sensor for determining blood pressure. It is generally desirable to remove sensors that may contact the blood.

The present invention aims to or at least address or ameliorate one or more of the disadvantages associated with the above mentioned prior art.

SUMMARY OF THE INVENTION

According to a first aspect the present invention consists of a system of controlling the speed of a rotary blood pump, wherein said system derives an estimated pulsatility index from speed, derives an estimated blood pressure from estimated pulsatility index; and maintains target blood flow rate near to or at a preset value by adjusting the speed.

Preferably, said system blood pressure is left atrial pressure.

Preferably, said estimated pulsatility index is calculated between beats of the cardiac cycle.

Preferably, said rotary blood pump is implanted within the body of a patient. Preferably, the preset value includes a range of values.

Preferably, said system additionally maintains the speed within a predetermined range.

According to a second aspect the present invention consists of a method of controlling the speed of a blood pump, wherein said method includes the steps of deriving an estimated pulsatility index from speed, then deriving an estimated blood pressure from estimated pulsatility index; and maintaining target blood flow rate near to or at a preset value by adjusting the speed.

According to a third aspect the present invention consists of a system of controlling the speed of a rotary blood pump, wherein said system derives an estimated pulsatility index from speed, derives an estimated blood pressure from estimated pulsatility index; and maintains pulsatility index within a predetermined range by adjusting the speed.

According to a fourth aspect the present invention consists of a control system for controlling the blood flow rate of a rotary blood pump said system comprising a measurement means for measuring the speed of the rotor, a first estimation means for estimating a pulsatility index as a function of speed, and a second estimation means for estimating blood pressure from said estimated pulsatility index, said system maintaining said blood flow rate at or near a predetermined value by adjusting said speed with respect to said estimated blood pressure.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

Figure 1:
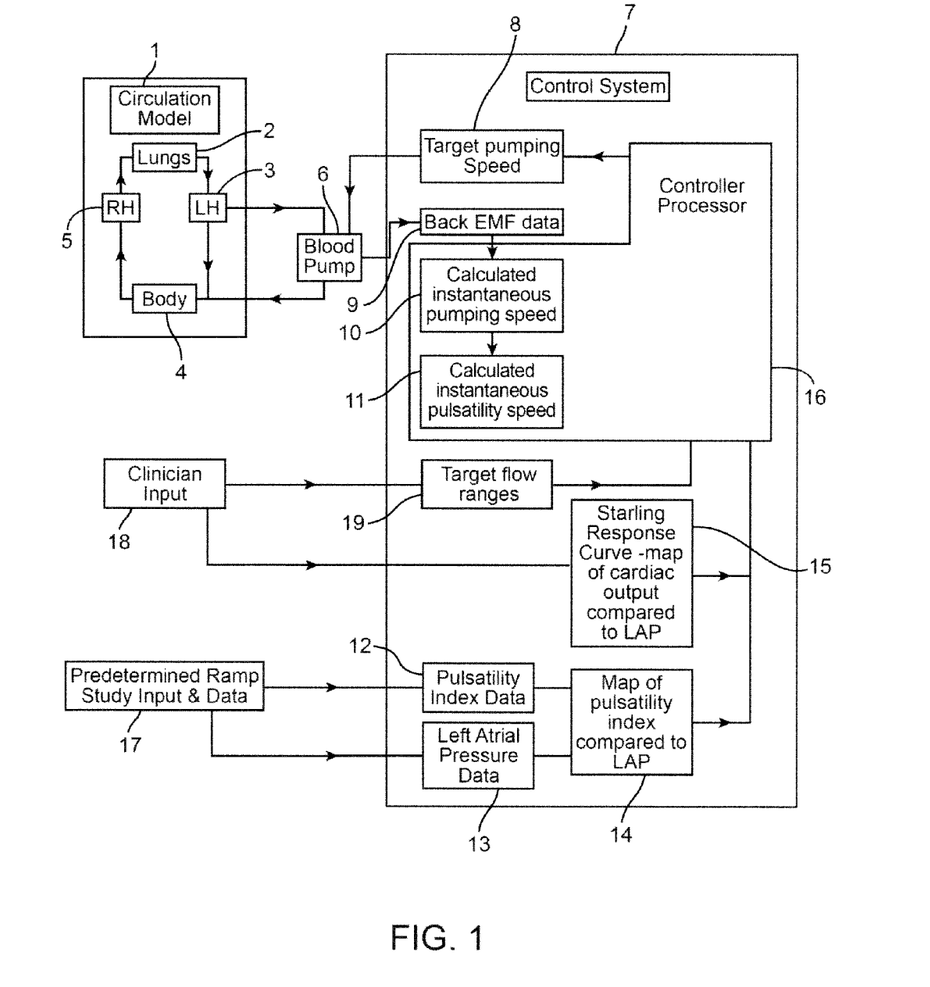
FIG. 1 depicts a schematic view of a first preferred embodiment of the present invention.

The first preferred embodiment of the present invention is depicted in FIGS. 1 to 4. In this first preferred embodiment, a control system 7 is connected to a rotary blood pump 6 in fluid communication with the circulatory system of a patient. In this embodiment, the circulatory system of the patient is depicted by circulation model 1. The circulation model 1 includes a left side of the heart 3 pumping blood to body 4 that generally includes legs, arms, extremities and other organs. The blood is then delivered from body 4 to the right side of the heart 5 wherein it is further pumped to the lungs 2 and eventually returned to the left side of the heart 3. Blood pump 6 is connected in parallel between the left ventricle of the heart, which is part of the left side of the heart 3, and a portion of the patient's aorta which is depicted in FIG. 1 as body 4.

Preferably blood pump 6 is a centrifugal type blood pump and may be implantable. The most preferred blood pump 6 is described within U.S. Pat. No. 6,227,797—Watterson et al. The specification of this aforementioned US patent is herein included within the present specification.

Blood pump 6 is preferably controlled by control system 7 that includes a controller processor 16. This controller processor 16 sets an appropriate target pumping speed 8 for the rotary blood pump 6 based on patient physiological and pump system parameters. Preferably blood pump 6 includes a DC brushless motor. Due to the motor designs and characteristics of DC brushless motors, as the magnetically charged impeller rotates within the housing of blood pump 6, a back EMF signal 9 is generated by the DC brushless motor in the stator coils of pump 6. The back EMF 9 is detected and measured by the control system 7 and generally is indicative of impeller (or rotor) position relative to the housing of pump 6. The controller processor 16 then calculates or derives the instantaneous pumping speed 10 from the back EMF signal 9 received from the blood pump 6.

The controller processor 16 may then utilise the instantaneous pumping speed 10 to calculate and derive an instantaneous pulsatility index 11 by using algorithms and methods well known in the field of rotary blood pump control.

Figure 2:
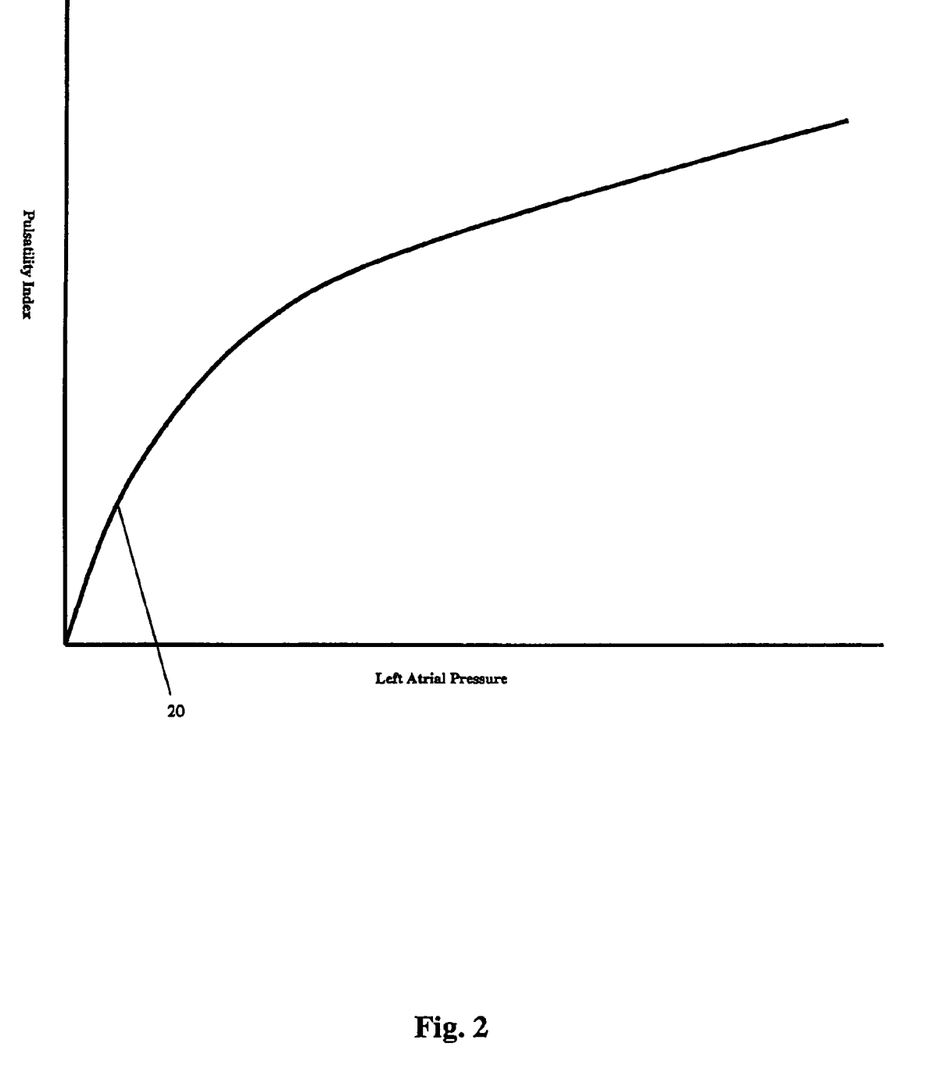
FIG. 2 depicts a graph of pulsatility index plotted against left atrial pressure.
Figure 3:
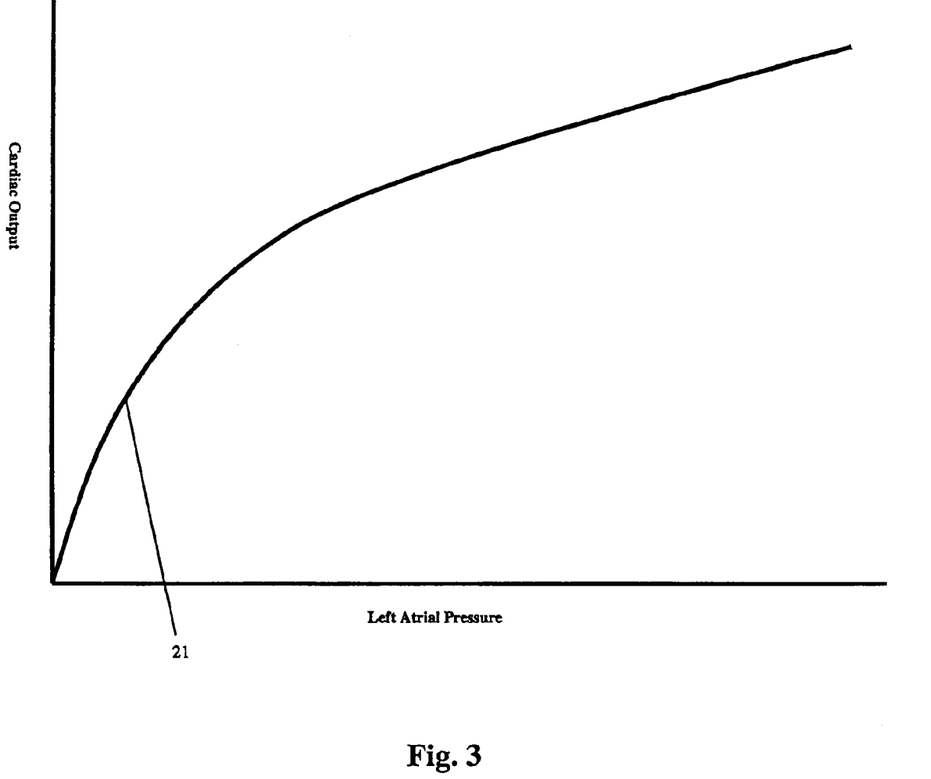
FIG. 3 depicts a graph of a Starling-like response curve wherein cardiac output is plotted against left atrial pressure.

The controller processor 16 also may receive input from a clinician or doctor regarding a preferred range of target blood flow rates 19 or a single preset value for a target most preferred target flow rate. Generally, the doctor or clinician will set these values at the time of implantation of blood pump 6. Target blood flow rate 19 preferably will differ dramatically between patients due to their differing physiological needs and differing extents of cardiac insufficiency or failure. Patients with cardiac myopathies or septum weaknesses may preferably have lower target ranges of blood flow rate 19 than healthy patients. The clinician or doctor may set these target blood flow rate 19 via a software or GUI interface preferably connected to control system 7 either through wireless connection or a direct cable connection (not shown). The clinician or doctor may also input 18 into controller processor 16, a Starling-like response curve 15. This curve 15 is a preferred map or graph of Left Atrial Pressure (herein referred to as 'LAP') plotted against different cardiac outputs. Cardiac output is usually described in terms in blood flow rates and in this specification this usual meaning has been adopted. An example of a Starling like response curve is depicted in FIG. 3 and shown as a plotted line 21. The Starling-like response curve demonstrates the relationship between cardiac output or flow rates and LAP. At the time of implantation of blood pump 6, the clinician or doctor may perform a ramp speed study 17 specific to the patient. The ramp study 17 generally requires a doctor or clinician to manually vary or ramp the pumping speed of blood pump 6 and simultaneously measure the left atrial pressure of the patient at different pumping speeds. The speed data is then converted into pulsatility indexes and the resulting data may be graphed into a curve or line 20 as depicted in FIG. 2. The curve 20 may be different for each patient and may have to be recalibrated at annual or biannual intervals to account for changes in patient health or physiology. Preferably, the LAP is measured by the clinician or doctor via a pressure sensor temporarily implanted into the left atrium of the patient's heart. Once the ramping study has been completed, the resulting data is stored within controller processor 16 and the sensor is preferably removed. The patient is generally not required to be permanently implanted with a pressure sensor and this may reduce risks and health complications related to use of implantable pressure sensors. When the resulting data is plotted on a graph as depicted in FIG. 2, the data forms a map 14 of pulsatility index plotted against LAP, and may use to estimate LAP from a given pulsatility index. The map 14 is then uploaded to controller processor 16.

The controller processor 16 then calculates the instantaneous pulsatility index 11 from the speed signal 10 of blood pump 6. The controller processor 16 then uses the map 14 and the calculated instantaneous pulsatility index 11 to estimate the instantaneous LAP. The instantaneous LAP is then compared to the Starling-like response curve 15 and controller processor 16 estimates an instantaneous cardiac output. Therefore the net result of the system is to compute or calculate an estimated instantaneous blood flow rate from the pumping speed of blood pump 6. The controller processor then determines whether the estimated flow rate is greater or less than the predicted or target flow rate and adjusts the pumping speed of blood pump 6 to provide the target flow rate. This system is continuously repeated.

Figure 4:
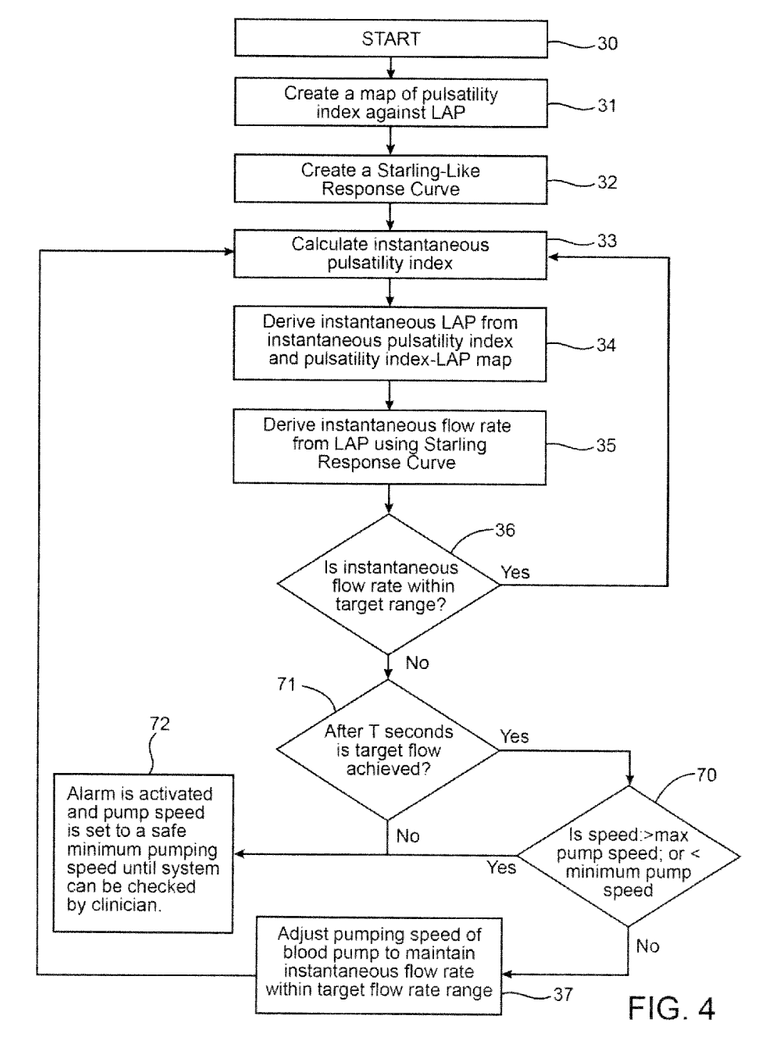
FIG. 4 depicts a schematic view of a flowchart depicting the decision tree used in the first preferred embodiment of the present invention.

A flow chart of the decision tree used in the first preferred embodiment of the present invention is depicted in FIG. 4. The system starts at step 30 by creating a map 31 of pulsatility index plotted against LAP. The system also preferably then in a second step 32 is inputted with a Starling-like response curve.

The next step 33 is where the system calculates an instantaneous estimate of the pulsatility index from the back EMF generated by blood pump 6. The system then may compare the pulsatility index with the map to derive an estimate of instantaneous LAP, in a further step 34. The system then utilises the LAP to derive an estimate of instantaneous blood flow rate in step 35.

The system then determines whether the instantaneous estimated blood flow rate is within a predetermined range of target blood flows set by a doctor or clinician or if it is at or near to a single preset flow rate. The term "near to" in this specification means sufficient proximal to the preset flow rate so as to facilitate the aim and function of the present embodiment and allows for uncertainty error around the preset value. If the instantaneous estimated blood flow is within the predetermined target ranges or preset value, the blood pump 6 is instructed to maintain its current speed of rotation or pumping.

If the estimated instantaneous blood flow is not within the target flow rates, the system takes a further step 37 to increase or decrease the pumping speed appropriately to facilitate the estimated instantaneous blood flow rate to come within the predetermined target ranges. Once the pumping speed has been amended the system repeats step 33, wherein the system calculates the instantaneous pulsatility index from the speed signal.

The described system may be constantly repeated or selectively turned on or off by a clinician or doctor. Additionally, the system may include timing delays between the steps described with reference to FIG. 4. Specifically, timing delays may be included within the gap of time between step 37 and step 33, wherein the system repeats. The timing periods may preferably be gaps of a few seconds.

For any of the embodiments, the system or control processor preferably calculates and derives the pulsatility index on a "beat to beat" basis which generally means that the pulsatility index is calculated on the average values determined between the beats of the patient's heart.

Furthermore, any of the above described embodiments may also include a further step or function within the clinician or doctor may set predetermined minima and maxima operating pumping speeds. The control system depicted in FIG. 4 includes steps, 70, 71 and 72 to manage minima and maxima pumping speeds. Preferably, controller processor 16 or the system will be instructed to operate pump 6 only within these speeds. If a minima or maxima speeds are reached, controller processor 16 will preferably not exceed the values and continue to operate pump 6 at the respective minima or maxima. Therefore, the system or controller processor 16 may also activate an alarm at this stage to alert the clinician, doctor or patient to the problem detected by the controller processor 16. These minima and maxima values may be able to limit the impact of ventricular collapse from over-pumping of the ventricle or oedemas from under-pumping the ventricle.

Figure 5:
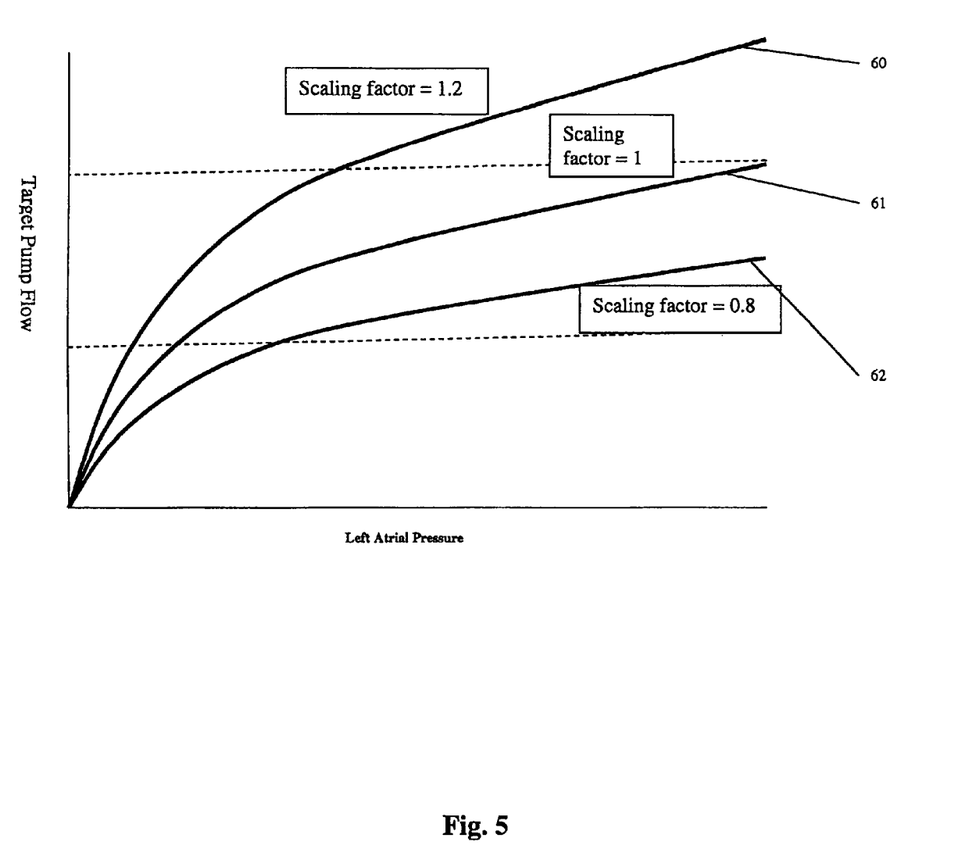
FIG. 5 depicts a graphical example of scaling factor to be with some embodiments of the present invention.

Additionally, series of preferred Starling relationships may be used to maintain pump flow within acceptable bounds. Preferably, an adaptive control mechanism may switch between different Starling relationships depending on the physiological conditions. This is to compensate for the changes in cardiac contractility in the circulation model 1. A scaling factor may be applied to compensate and adjust the desired Starling curve (Target Pump Flow vs. LAP or Target Pump Flow vs. PI). This scaling factor is demonstrated in FIG. 5 wherein a relatively high scaling factor is shown by line 60; the normal starling response is shown by line 61 wherein the scaling factor is 1; and a relatively low scaling factor is depicted in FIG. 5 by line 62. In this embodiment, the relatively high scaling factor may be 1.2 and the relatively low scaling factor is 0.8. However the scaling factor is dependent on the physiological conditions of the patient and may be variable.

Preferably, alterations to the scaling factor aim to keep pump flow within the acceptable range of pump flow.

Figure 6:
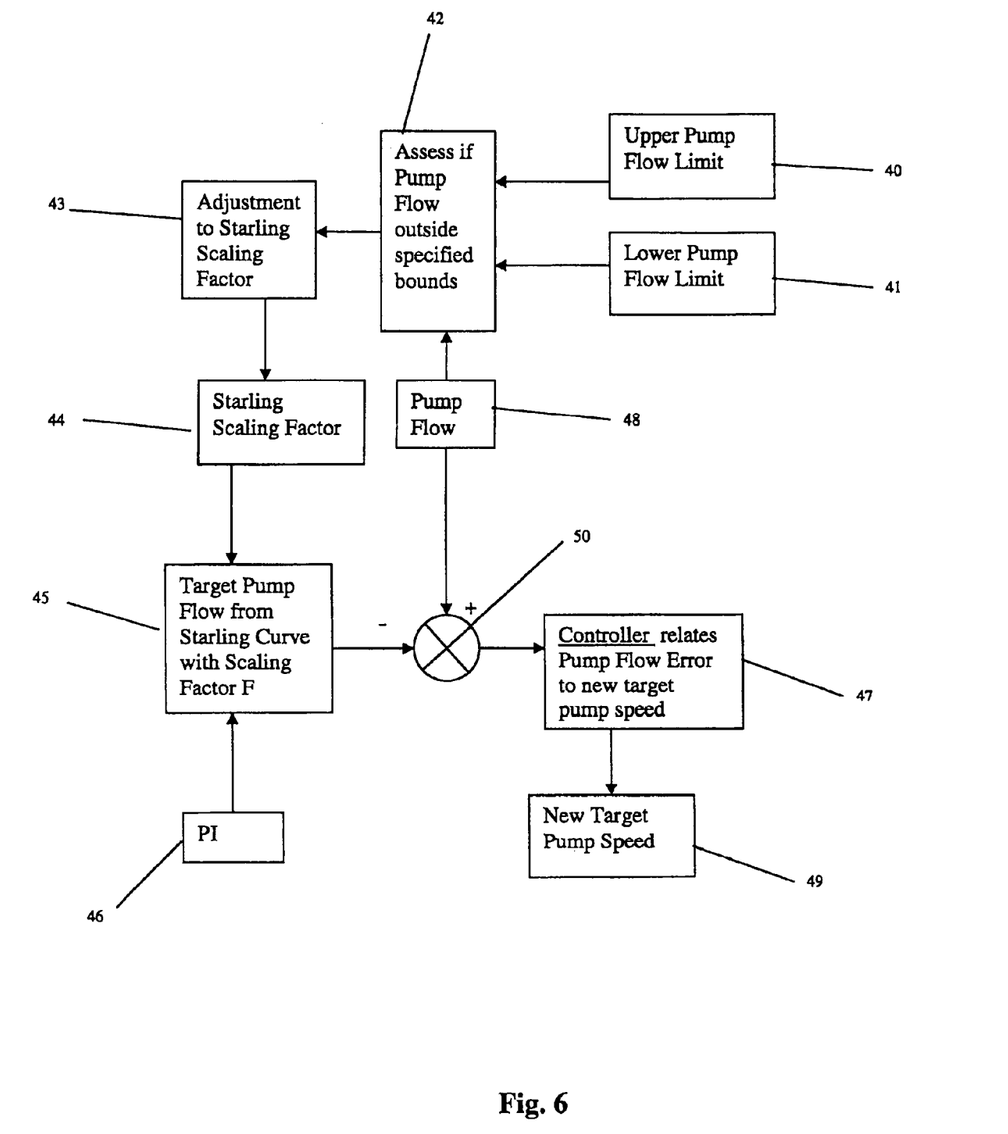
FIG. 6 depicts a flow chart of methodology used by a further embodiment of the present invention.

In FIG. 6, an embodiment of a preferred system for using the scaling factor is demonstrated. A clinician sets an upper 40 and lower flow rate limit 41. These are preferably entered using a similar means as described with reference to the previous 10 embodiments.

The controller in a first step 42 assesses if the current pump flow rate is within the upper 40 and lower limits 41.

If pump flow is predominantly above the upper bound as controller processor operates to abide by the current scaling factor on the Starling curve, then the scaling factor on the target Starling curve is lowered. Conversely if the pump flow is predominantly below the lower bound then this scaling factor is increased.

Figure 7:
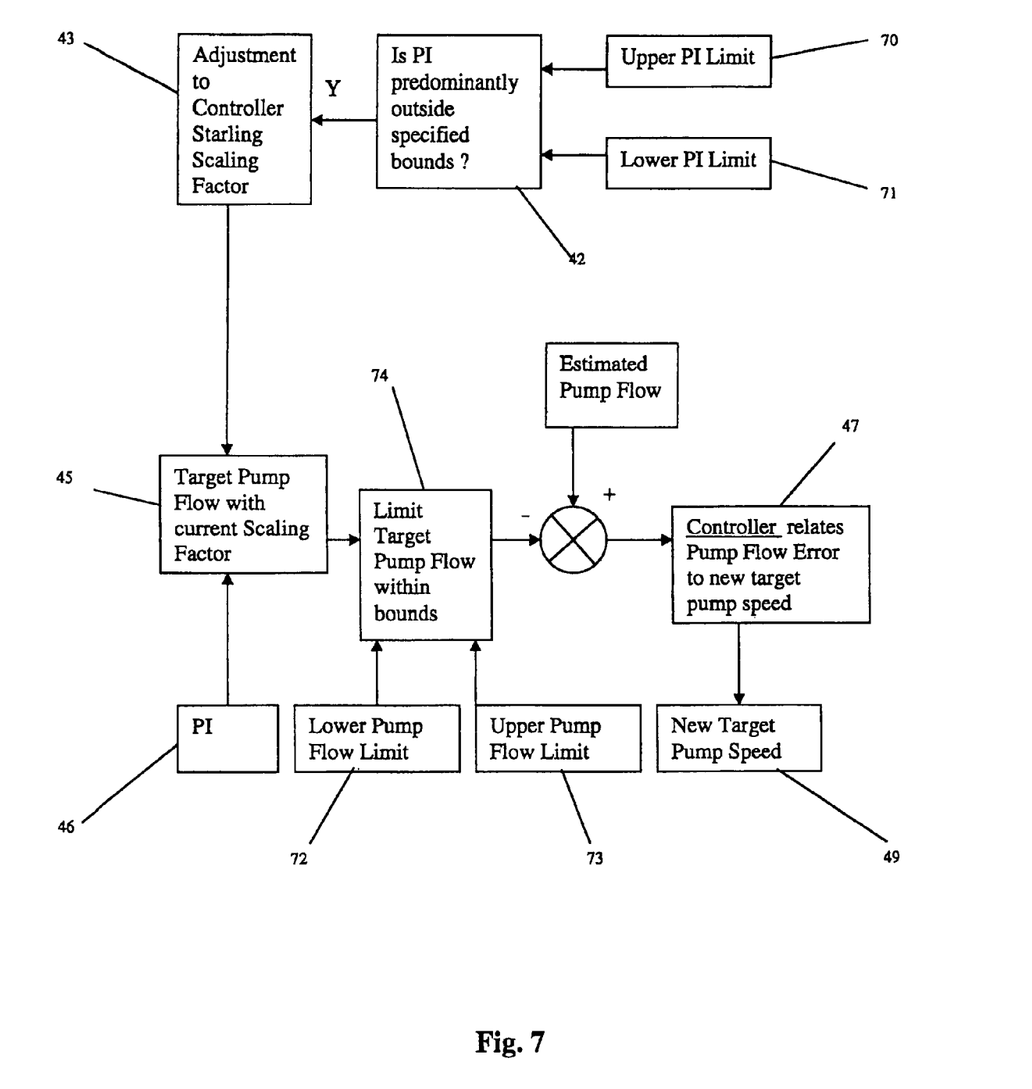
FIG. 7 depicts a further flow chart of methodology used by a further embodiment of the present invention.

A further embodiment is depicted in FIG. 7, this embodiment is similar to the embodiment depicted in FIG. 5. However, in the embodiment of FIG. 7 the system includes upper 70 and lower 71 pulsatility index limits. The controller processor in a first step 42 determines whether the pulsatility index (herein referred to as 'PI') is within the upper and lower PI limits 70 and 71. Additionally, the controller processor includes an additional step 74 between steps 45 and 50, wherein the additional step 74 limits the target pump flow within further flow limits, which have been preset into the system as upper and lower flow limits 72 and 73.

In this embodiment, the controller adjusts to changes in left ventricle contractility by adjusting a scaling factor (see FIG. 5) which is applied to the relationship between the target pump flow and PI. In situations where the PI is generally above the upper PI limit 70 as the controller operates to maintain the target pump flow, then the scaling factor is increased until PI falls to levels within the specified limits 70 and 71.

A person skilled in the art will also appreciate that the preferred system of this embodiment may function in the inverse manner, if the PI generally falls below the lower PI limit 71.

The above descriptions detail only some of the embodiments of the present invention. Modifications may be obvious to those skilled in the art and may be made without departing from the scope and spirit of the present invention.

The invention claimed is:

1. A method for controlling a blood pump for a patient, the blood pump having a motor, comprising:
    computing a pulsatility index from a motor speed;
    determining an atrial pressure from the computed pulsatility index based on pre-stored atrial pressure data for the patient;
    estimating a cardiac output based on the atrial pressure and a map of atrial pressures for different cardiac output; and
    comparing the estimated cardiac output to a desired target range for the cardiac output and if the estimated cardiac output is not within the desired target range sending a control signal to adjust the motor speed to achieve the desired target range.

2. The method of claim 1, wherein the estimated cardiac output is an estimated blood flow rate.

3. The method of claim 1, wherein the pre-stored atrial pressure data for the patient is obtained by ramping the motor speed among a plurality of motor speeds while simultaneously recording the patient's atrial pressure at each of the plurality of motor speeds using a pressure sensor temporarily implanted within the patient.

4. The method of claim 1, wherein the cardiac output is estimated using pre-stored Starling-like response data.

5. The method of claim 1, wherein the atrial pressure is a left atrial pressure (LAP).

6. The method of claim 1, wherein the pulsatility index is computed from average values of motor speed between the beats of the patient's heart.

7. The method of claim 1, further including the step of limiting the motor speed to a predetermined maximum and minimum motor speed for the patient and if the maximum or minimum motor speeds are reached, sounding an alarm to indicate a possible over-pumping or under-pumping condition of the patient's ventricle.

8. The method of claim 1, wherein the estimating a cardiac output for the atrial pressure further includes:
    selecting among a plurality of maps of atrial pressures for different cardiac output, each of the plurality of maps corresponding to a different physiological condition of the patient, and
    estimating the cardiac output from the selected map of atrial pressures for different cardiac output.

9. The method of claim 8, wherein the plurality of maps include at least a first map having a first scale factor, and a second map having a second scale factor, wherein the scale factors are dependent on the patient's physiological condition.

10. The method of claim 9, wherein the scale factors are selected to maintain a pump flow within an acceptable range of pump flow.

11. A controller adapted for controlling a blood pump for a patient, the blood pump having a motor, the controller comprising:
    a processor configured for computing a pulsatility index from a signal received by the controller from the blood pump,
    the processor being further configured for determining an atrial pressure using the computed pulsatility index and pre-stored atrial pressure data for the patient, and estimating a cardiac output using a map of atrial pressures for different cardiac output;
    wherein the controller is configured to send a signal to the motor to adjust the pump speed when the estimated cardiac output is not within a desired range of cardiac output for the patient.

12. The controller of claim 11, wherein the estimated cardiac output is an estimated blood flow rate.

13. The controller of claim 11, wherein the cardiac output is estimated using pre-stored Starling-like response data.

14. The controller of claim 11, wherein the atrial pressure is a left atrial pressure (LAP).

15. The controller of claim 11, wherein the controller is configured for computing the pulsatility index from a measured back EMF of the motor.

16. The controller of claim 11, wherein the controller is configured for sending control signals that limit the motor speed to within a range defined by a predetermined maximum and minimum motor speed for the patient, the controller further including an alarm that is activated if the maximum or minimum motor speeds are reached, the alarm indicating a possible over-pumping or under-pumping condition of the patient's ventricle.

17. The controller of claim 11, wherein the controller includes an adaptive control mechanism for selecting among a plurality of maps of atrial pressures for different cardiac output based on the physiological condition of the patient.

18. The controller of claim 17, wherein the plurality of maps include at least a first map having a first scale factor, and a second map having a second scale factor, wherein the scale factors are dependent on the patient's physiological condition.

19. The controller of claim 18, wherein the scale factors are selected to maintain a pump flow within an acceptable range of pump flow.

20. The controller of claim 17, wherein the adaptive control mechanism selects a first one of the plurality of maps if the patient's cardiac output is predominantly above or below an estimated cardiac output according to a second one of the plurality of maps and the determined atrial pressures.

* * * * *